United States Patent [19]

Esser et al.

[11] Patent Number: 4,506,014

[45] Date of Patent: Mar. 19, 1985

[54] PLASMID PAC 1, A PROCESS FOR OBTAINING IT AND ITS USE

[75] Inventors: Karl Esser, Bochum; Walter Minuth, Frankfurt am Main, both of Fed. Rep. of Germany

[73] Assignee: Hoechst Aktiengesellschaft, Frankfurt am Main, Fed. Rep. of Germany

[21] Appl. No.: 435,243

[22] Filed: Oct. 19, 1982

[30] Foreign Application Priority Data

Oct. 21, 1981 [DE] Fed. Rep. of Germany ....... 3141691

[51] Int. Cl.$^3$ .................... C12N 15/00; C12N 1/00; C12P 35/06
[52] U.S. Cl. ................................ 435/172.3; 435/317; 435/49; 935/29; 935/60
[58] Field of Search ............... 435/172, 317, 49, 172.3

[56] References Cited

U.S. PATENT DOCUMENTS 3,082,155  3/1963  Kelly et al. ........................... 435/49

FOREIGN PATENT DOCUMENTS 92388  10/1983  European Pat. Off. .

OTHER PUBLICATIONS

Broda, Plasmids, Freeman and Company, San Francisco, pp. 5–22 and 140, (1979).
Minuth et al., Current Genetics 5, 227–231, (1982).

*Primary Examiner*—Alvin E. Tanenholtz
*Attorney, Agent, or Firm*—Curtis, Morris & Safford

[57] ABSTRACT

Plasmid pAC 1, which is obtained from *Acremonium chrysogenum* ATCC 14553 and has a contour length of about 6.7 μm and a molecular size of about 20.9 kilobases (=kb), a process for obtaining it and its use for preparing a hybrid vector which promotes the biosynthesis of β-lactam antibiotics.

4 Claims, No Drawings

PLASMID PAC 1, A PROCESS FOR OBTAINING IT AND ITS USE

The invention relates to the plasmid pAC 1, a process for obtaining it from *Acremonium chrysogenum* ATCC 14553 and its use for preparing a hybrid vector which promotes the biosynthesis of β-lactam antibiotics.

The application of genetic engineering methods to strains of fungi producing antibiotics has become increasingly important in recent times. This has the object of obtaining genetically modified strains of fungi which exhibit a greater productivity in forming antibiotics. However, this object can only be achieved successfully with genetic engineering methods when a plasmid is available which is not immediately eliminated again from the host cell, which is to be genetically improved as is frequently observed for microorganisms which are not related to one another.

It has been disclosed that certain strains of various species of Acremonium are employed for the preparation of cephalosporins. Since, however, it has not yet been possible to find plasmids either in species of Acremonium or in other closely related strains of fungi, it has not hitherto been possible to employ genetic engineering methods to obtain strains having an increased cehalosporin production.

It has now been found, surprisingly, that a plasmid occurs in the strain *Acremonium chrysogenum* ATCC 14553, which plasmid has a contour length of about 6.7 μm and a molecular size of about 20.9 kilobases (=kb). This plasmid has been given the name pAC 1.

The plasmid pAC 1 can be characterized on agarose gels by endonucleolytic cleavage with restriction enzymes. By this means, the number and size of the particular fragments can be determined. Thus, the restriction endonuclease Bgl II cleaves this plasmid into six fragments having the sizes 5.10, 4.75, 4.30, 3.50, 2.15 and 1.05 kb.

In contrast, the restriction endonuclease Eco R I divides the plasmid pAC 1 into five fragments having the sizes 8.1, 4.7, 4.4, 2.6 and 1.3 kb.

The restriction endonuclease Hpa I, on the other hand, cleaves the plasmid into nine fragments having the sizes 5.61, 4.30, 3.50, 2.72, 1.35, 1.25, 0.82, 0.74 and 0.61 kb.

In contrast, no cleavage has yet been observed due to the action of the restriction endonucleases Hind III, Sal I and Kpn I.

Isolation of plasmid pAC 1 from cultures of *Acremonium chrysogenum* ATCC 14553 is complicated, primarily because, in addition, nuclear DNA (=nDNA) and mitochondrial DNA (=mtDNA), the latter of similar density and contour length, also occur in the cell, from which the plasmid pAC 1 must be carefully separated. However, it has emerged that the problem of purification of plasmid pAC 1 can be solved when the total DNA obtained from protoplast lysates or mechanically ruptured mycelia of *Acremonium chrysogenum* ATCC 14553 is prepurified by cesium chloride centrifugation, the circular DNA, comprising plasmid DNA and mitochondrial DNA, is separated therefrom by chromatography, for example on hydroxyapatite and the plasmid DNA is finally isolated and purified by several, preferably three, consecutive cesium chloride centrifugations. Protoplasts or mycelia which have been ruptured mechanically after freezing in liquid nitrogen serve as the starting material.

In the following text, preferred embodiments of the invention are illustrated in more detail.

Liberation of the total DNA is achieved by incubation with a surfactant, such as sodium dodecyl sulfate (=SDS), and a protein-degrading enzyme, such as proteinase K; it is separated from the other cellular constituents by an ethanol precipitation and a cesium chloride gradient centrifugation. By chromatography on hydroxyapatite, using particular salt concentrations, the total DNA is initially specifically bound (and thus freed of residual impurities, particularly RNA and carbohydrates), then the lower molecular weight circular DNA (mt- and pl-DNA) is specifically eluted, whilst the nuclear DNA remains bound on the column. Separation of mitochondrial DNA, which is very similar with respect to structure and contour length, from plasmid DNA is carried out by taking advantage of the slight difference in density by means of a small number of preparative ultracentrifugation steps in cesium chloride gradients. The degree of purity of the preparation is checked by restriction analysis and electronmicroscopic imaging.

The plasmid pAC 1 is particularly suitable for forming a hybrid vector which can be introduced into Acremonium species. This is because it has emerged that all the plasmids hitherto known can only be established in relatively few host cells. The greatest chances of successful cloning always exist when the hybrid vector is introduced into a closely related host cell. Thus, in this context, the relationship between the cephalosporin-producing strains provides a very good basis.

In order to prepare the hybrid vector, the same genetic engineering methods are applied which have already been employed earlier for *Escherichia coli* plasmids and are also applied to Streptomycetes by M. Bibb, J. C. Schottel and S. N. Cohen, Nature 284, 526–531 (1980) and C. J. Thompson, J. M. Ward and D. A. Hopwood, Nature 286, 525–527 (1980).

By these known processes, not only genes which carry antibiotic resistance can be inserted into the plasmid pAC 1 in some of the cleavage sites obtained with the abovementioned restriction endonucleases, but also genes which bring about an increase in antibiotic production. The hybrid plasmids thus obtained are, according to all observations made hitherto, just as viable and capable of reproduction in Acremonium cells as the initial plasmid.

The invention is further illustrated by the following example:

EXAMPLE

The starting strain for the isolation of the plasmid DNA is the strain *Acremonium chrysogenum* ATCC 14553. The mycelium of this strain was cultured by shaking for about 48 hours in a complete liquid medium of the following composition:

Sucrose—3.0 g
Dextrin (white)—15.0 g
NaCl—0.5 g
$K_2HPO_4$—0.5 g
$MgSO_4.7H_2O$—0.5 g
$FeSO_4.7H_2O$—0.01 g
Trypticase-soy broth (Difco)—5.0 g
Meat extract (Difco)—1.0 g
Yeast extract (Difco)—2.0 g
Agar (Serva)—20 g
Distilled $H_2O$—ad 1,000 ml.

This medium had previously been sterilized at 121° C. for 20 minutes. In this case, the pH set up was 7.0 to 7.2.

After 48 hours, the mycelium was harvested through gauze and ruptured under liquid nitrogen by the process described by U. Stahl et al. [Molec. Gen. Genet. 178,639 et seq. (1980)]. About 30 g of mycelium were employed for the further process.

However, the rupturing of the cells can also be carried out using enzymes. For this purpose, the mycelium separated off from the culture solution was washed twice with distilled water, suspended in an isotonic neutral solution containing 0.5% by weight of 2-mercaptoethanol and incubated in a stationary manner at 30° C. for 30 minutes. Thereafter, the mycelium was washed with an isotonic neutral solution. Then 12 mg/ml of the cytophage enzyme $L_1$ and 2 mg/ml of zymolase were allowed to act on this mycelium in an isotonic neutral solution for about 3 hours, with gentle shaking and at a temperature of 30° C. The protoplasts were then separated from the remaining pieces of mycelium by filtration (glass wool filter) and washed twice by centrifugation in isotonic solution for five minutes.

Then, ethylenediaminetetraacetate, as a nuclease inhibitor, was added to the protoplast suspension up to a final concentration of 60 mM. Thereafter, in order to liberate the total DNA, sodium dodecyl sulfate, to a final concentration of 1%, and proteinase K (Merck), to a final concentration of 0.02% by weight, were initially added, the mixture was then allowed to stand at 37° C. for 30 minutes and finally incubated at 70° C. for 15 minutes. The crude lysate was clarified by centrifugation (10 minutes at 10,000×g and 4° C.) and then dialysed for 15 hours against a buffer composed of 50 mM trishydroxymethylaminomethane and 20 mM ethylenediaminetetraacetate. The total DNA was precipitated by the addition of 2 volumes of ethanol and centrifuged off after standing at −20° C. for 15 hours (8 minutes at 3,000×g at −20° C.) and prepurified by isopycnic gradient centrifugation in a cesium chloride solution, which is adjusted to the density of 1.700 (21 hours at 45,000 rpm in a Sorvall rotor TV 865 at 15° C.) The DNA bands were obtained using an Isco Fractionator.

In order to separate the circular DNA, which comprises plasmid DNA and mitochondrial DNA, from the total DNA, the mixture was dialyzed against a buffer composed of 50 mM trishydroxymethylaminomethane, 20 mM ethylenediamine tetraacetate and 240 mM sodium dihydrogen phosphate and having a pH of 6.7. The dialysate was chromatographed on hyroxyapatite by the process described by Colman et al. [Eur. J. Biochem. 91, 303 et seq. (1978)]. In this process, the total DNA was initially bound to a column of 2 g of hydroxyapatite, and then the circular DNA was washed out with buffer solutions, whilst the nuclear DNA remained bound to the apatite.

Separating off the mitochondrial DNA and thus purifying the plasmid DNA was carried out by three consecutive isopycnic gradient centrifugations in a cesium chloride solution which was adjusted to a density of 1.700 (44 hours at 32,000 rpm in a Sorvall rotor TV 865 at 15° C.).

We claim:

1. A plasmid, pAC 1, isolated from *Acremonium chrysogenum* ATCC 14553 and having a contour length of about 6.7 microns and a molecular size of about 20.9 kilobases, which plasmid is divided into six fragments having the sizes 5.10, 4.75, 4.30, 3.50, 2.15 and 1.05 kilobases by the restriction endonucleaase Bgl II, is divided into five fragments having the sizes 8.1, 4.7, 4.4, 2.6 and 1.3 kilobases by the restriction endonuclease Eco R I, and is divided into nine fragments having the sizes 5.61, 4.30, 3.50, 2.72, 1.35, 1.25, 0.82, 0.74, and 0.61 kilobases by the restriction endonuclease Hpa I.

2. A process for obtaining the plasmid pAC 1, which comprises prepurifying, by cesium chloride centrifugation, the total DNA obtained from protoplast lysates or mechanically ruptured mycelia of *Acremonium chrysogenum* ATCC 14553, separating out therefrom the circular DNA, comprising plasmid DNA and mitochondrial DNA, by chromatography and finally isolating and purifying the plasmid DNA by several consecutive cesium chloride centrifugations.

3. The process as claimed in claim 2, wherein the circular DNA is separated off from the nuclear DNA by chromatography on hydroxyapatite.

4. A process for preparing a hybrid vector which comprises cleaving the plasmid as claimed in claim 1 by a restriction endonuclease and inserting into the cleavage sites a gene which promotes the biosynthesis of β-lactam antibiotics.

* * * * *